(12) United States Patent
Lebon et al.

(10) Patent No.: US 6,794,411 B1
(45) Date of Patent: Sep. 21, 2004

(54) DRINKABLE IBUPROFEN PHARMACEUTICAL SUSPENSION

(75) Inventors: Christophe Lebon, Rouvres (FR); Emmanuel Guerin, Paris (FR); Pascal Suplie, Montaure (FR)

(73) Assignee: Laboratoire des Produits Ethiques Ethypharm, Houdan (FR)

( * ) Notice: Subject to any disclaimer, the term of this patent is extended or adjusted under 35 U.S.C. 154(b) by 0 days.

(21) Appl. No.: 09/958,143

(22) PCT Filed: Apr. 6, 2000

(86) PCT No.: PCT/FR00/00869

§ 371 (c)(1), (2), (4) Date: Nov. 6, 2001

(87) PCT Pub. No.: WO00/59467

PCT Pub. Date: Oct. 12, 2000

(30) Foreign Application Priority Data

Apr. 6, 1999 (FR) ............................................. 99 04251
Apr. 5, 2000 (FR) ............................................. 00 04359

(51) Int. Cl.[7] ............................................... A61K 31/19
(52) U.S. Cl. ........................ 514/568; 514/570; 424/439
(58) Field of Search ............................. 514/568, 570; 424/439

(56) References Cited

U.S. PATENT DOCUMENTS

| | | | |
|---|---|---|---|
| 5,110,606 A | 5/1992 | Geyer et al. | |
| 5,602,182 A | 2/1997 | Popli et al. | |
| 5,674,533 A | 10/1997 | Santus et al. | |
| 5,925,376 A | * | 7/1999 | Heng ........................ 424/451 |
| 6,261,602 B1 | 7/2001 | Calanchi et al. | |

FOREIGN PATENT DOCUMENTS

| | | |
|---|---|---|
| EP | 0 378 137 | 7/1990 |
| EP | 0 413 533 | 2/1991 |
| EP | 0 298 740 | 1/1992 |
| EP | 0468232 * | 1/1992 |
| EP | 0 468 232 A2 | 1/1992 |
| EP | 0559463 * | 9/1993 |
| EP | 0 559 463 A1 | 9/1993 |
| EP | 0 405 930 | 8/1994 |
| EP | 0 524 180 | 4/1995 |
| EP | 0 717 992 | 6/1996 |
| EP | 0 556 057 | 10/1996 |
| EP | 0 664 701 | 9/1997 |
| FR | 2 615 101 | 11/1988 |
| FR | 2 771 291 | 5/1999 |
| FR | 2 771 292 | 5/1999 |
| JP | 91-83922 | 4/1991 |
| JP | 10-182 449 | 7/1998 |
| WO | WO 85 03000 | 7/1985 |
| WO | WO 91-16043 | 10/1991 |
| WO | WO 93-12771 | 7/1993 |
| WO | WO 94-05260 | 3/1994 |
| WO | WO 94-12180 | 6/1994 |
| WO | WO 94-25006 | 11/1994 |
| WO | WO 95-05166 | 2/1995 |
| WO | WO 95/17177 A1 | 6/1995 |
| WO | 95/17177 * | 6/1995 |
| WO | WO 96-01628 | 1/1996 |
| WO | WO 96-22762 | 8/1996 |
| WO | WO 96-35436 | 11/1996 |
| WO | WO 98-17250 | 4/1998 |

* cited by examiner

*Primary Examiner*—Phyllis G. Spivack
*Assistant Examiner*—C. Delacroix-Muirheid
(74) *Attorney, Agent, or Firm*—Foley & Lardner

(57) ABSTRACT

The invention relates to a drinkable ibuprofen solution wherein the soluble fraction of the active ingredient contained therein is less than 10% by weight in relation to the weight of the suspension.

11 Claims, No Drawings

DRINKABLE IBUPROFEN PHARMACEUTICAL SUSPENSION

This application is a 371 of application serial number PCT/FR00/00869 filed Apr. 6, 2000.

The present invention relates to an oral pharmaceutical ibuprofen composition intended for facilitated oral administration.

The oral administration of solid forms such as tablets can prove difficult or even dangerous for children and the elderly, who prefer chewable tablets, tablets which dissolve in the mouth or in a spoon of water, granules, powders, solutions or suspensions.

The active ingredients incorporated into these types of formulations sometimes have a bitter taste which persists for a long time and which cannot be effectively masked by the addition of a sweetener or a flavoring. However, the taste and the aftertaste are important criteria for the acceptance of the medicament by the patient.

In the oral suspensions of bitter active ingredient already described in the prior art, the active ingredient is generally coated with a lipid substance, either directly or after incorporation into a core. The lipid substances used are for example a partially hydrogenated vegetable oil (EP 670 722), stearic acid and/or palmitic acid (FR 2 615 101), glyceryl tripalmitate (EP 664 701), or a mixture of glyceryl monostearate and beeswax in the proportions 9/1 (EP 769 948).

Ibuprofen is an active ingredient with a bitter taste which has been the subject of numerous studies in order to formulate it in stable compositions in which its taste is masked.

A prior art solution consists in coating the ibuprofen-containing granules with a polymer intended to mask its bitter taste. This polymer is for example a phthalate (WO 91/16043), a vinyl acetal (JP 91/83922), a cellulose acetate phthalate (WO 95/05166) or a methacrylic acid copolymer (EP 524 180).

Another prior art solution consists in preparing an aqueous suspension of ibuprofen. This suspension contains either a lipid substance and a surfactant (WO 94/25006, U.S. Pat. No. 5,110,606, WO 96/22762, WO 94/05260), or a suspending agent, such as a polysaccharide (JP 98/182 449), a mixture of cellulose and of xanthan gum (EP 556 057), a mixture of polyethylene glycol and of sodium carboxymethyl cellulose (U.S. Pat. No. 5,602,182), a mixture of xanthan gum and of pregelatinized starch (EP 405 930), a mixture of xanthan gum, of microcrystalline cellulose and of carboxymethyl cellulose (EP 298 740).

The subject of the present invention is an oral pharmaceutical ibuprofen suspension which is provided in a dry form, reconstitutable in liquid form, or which is ready for use in liquid form comprising a liquid phase in which ibuprofen in a solid state is dispersed, characterized in that the solubilized fraction of ibuprofen in the liquid phase is less than 10% by weight relative to the total quantity of ibuprofen, preferably less than 5% by weight, preferably less than 1% by weight.

The active ingredient is in the form of crystals, preferably crystals of less than 500 microns in size, or formulated in granules. The crystals may or may not be coated with a film-forming substance.

The active ingredient is dispersed in the liquid phase so as to obtain a stable and homogeneous suspension.

The granules are optionally coated with a material intended either to allow the modified release of the active ingredient embedded on a neutral support, or to mask the taste of said active ingredient, or to avoid solubilizing the active ingredient in the liquid phase of the suspension.

The granules have a final size of between 50 and 1 000 microns, preferably between 200 and 600 microns. They consist of an inert core having a size substantially between 100 and 350 microns and a spherical shape onto which the active ingredient is applied by means of a binder or by mere absorption if the active ingredient is in solution.

The granules are for example obtained by coating the active ingredient(s) onto a neutral support consisting of sugar and starch.

The coating of the neutral support with the active ingredient may be carried out according to several techniques, such as dusting, spraying of a solution or suspension of the active ingredient, or any other conventional technology known to persons skilled in the art.

The neutral support coated with active ingredient is then optionally coated with a polymer film consisting of a single polymer or of a combination of several polymers or coated with a succession of different layers of polymer, depending on the expected effect. This step may be carried out using the various excipients and technologies well known to persons skilled in the art. Aqueous solvents will preferably be used.

The oral pharmaceutical suspension according to the invention advantageously consists of a liquid phase which is aqueous or consists of a mixture of water with a cosolvent, for example an oil, propylene glycol, glycerin or a solution of sorbitol.

The suspension according to the invention may also be provided in the form of a dry mixture of excipients and of active ingredient, which may be freshly prepared by simply adding water. The active ingredient is then dispersed by stirring manually, so as to obtain a homogeneous and stable formulation.

The dry suspension is prepared by mixing the active ingredient, in the form of crystals or granules, and the suspension adjuvants. It may be granulated according to various conventional granulation techniques well known to persons skilled in the art, or may result from simple physical mixing of the various components.

The powder is then distributed into bottles. The bottles are sufficiently large for the quantity of water needed for the reconstitution to be added.

The oral pharmaceutical suspension according to the invention contains at least one viscosity agent, at least one filler and at least one preservative.

The viscosity agent is chosen from pharmaceutically acceptable viscosity agents, for example xanthan gum, hydroxypropylmethyl cellulose, methyl cellulose, carageenan, carboxymethyl cellulose, microcrystalline cellulose, polyvinylpyrrolidone and carbomers.

The viscosity agent is advantageously a carbomer. Carbomers are acrylic acid polymers containing interchain allylsucrose and allypentaerythritol groups. A grade is preferably chosen whose synthesis does not require the use of benzene as solvent, such as carbomer 971P. In addition, carbomers have the advantage of being used in small quantities.

The viscosity agent represents 0.1 to 10%, preferably 0.1 to 2.5%, by weight relative to the weight of the suspension.

Throughout the application, in the expression "% by weight relative to the weight of the suspension", there is understood to mean a suspension in liquid form which has been optionally reconstituted.

The filler represents 10 to 70%, preferably 30 to 55%, by weight relative to the weight of the suspension. It is chosen from sucrose or noncariogenic agents such as sorbitol, xylitol, mannitol, lactitol or maltodextrins.

The preservative represents 0.05 to 3%, preferably 0.1 to 1%, by weight relative to the weight of the suspension.

The preservative or the mixture of preservatives makes it possible to maintain the microbiological integrity of the suspension and to satisfy the regulatory requirements relating to the enumeration of total and specific microorganisms and to the study of efficacy of the preservatives.

A mixture of preservatives is preferably chosen so as to obtain a synergy of antibacterial effects.

At least one of the preservatives is chosen from the esters of parabens or the corresponding salts.

The oral suspension according to the invention may contain, in addition, at least one agent chosen from an alkalinizing or acidifying agent, a flavoring, an antioxidant, a coloring, a lubricant and a sweetener.

The sweetener is chosen based on its higher sweetening power than sucrose, such as aspartame, saccharin, sodium cyclamate and mixtures thereof.

The flavoring may be of natural or synthetic origin. It represents 0.1 to 3% by weight relative to the weight of the suspension.

The coloring is a natural or synthetic pigment, chosen based on the suspension flavor. In the case of a strawberry flavor, cochineal red or Ponceau red 4R will be preferably chosen.

The lubricant is, for example, talc, aluminum oxide or silica.

The following examples illustrate the present invention without limiting the scope thereof.

EXAMPLE 1

Suspension of Ibuprofen Crystals

A batch corresponding to 300 liters of suspension, that is 2 000 bottles of 150 ml, is prepared from the following formula

| COMPONENTS | MANUFACTURING FORMULA |
|---|---|
| Ibuprofen | 6.00 kg |
| Sucrose | 115.50 kg |
| Noncrystallizable sorbitol at 70% | 18.30 kg |
| Carbomers (Carbopol ® 971 P) | 0.51 kg |
| Parabens (Nipasept ® base) | 0.35 kg |
| Strawberry flavor | 0.35 kg |
| Cochineal Red A coloring | 0.010 kg |
| Sodium hydroxide (1N solution) | 2.00 kg |
| Purified water | 208.30 kg |

Preparation No. 1

Water (127 kg) is introduced into the 200 l tank at room temperature and then the Carbopol® 971P is dispersed in small quantities in the water.

The mixture is homogenized with a deflocculating turbine for 1 hour at 1 500 rpm and then for 4 hours at 800 rpm.

Preparation No. 2

A 400 liter jacketed tank is heated to 80° C. and water (75 kg) is introduced at 80° C. The temperature of the water is maintained between 75° C. and 80° C. during the preparation.

The three-blade AE 200 mm turbine is mounted on the RAYNERI DIRECT T 80 stirrer.

The stirring is started and maintained (200 rpm) throughout the preparation. The preservatives and the flavor are dispersed until they are completely dissolved.

The sucrose is added and allowed to dissolve completely (the clarity of the solution is checked), the 70% liquid sorbitol is added and then the container is rinsed with water (6.3 kg).

The coloring is added and the stirring is continued until a clear solution is obtained. The the jacket is cooled and the temperature of the solution is allowed to return to 35° C.

In the 400 l tank, the preparation No. 1 is poured, with stirring (200 rpm), into the preparation No. 2. The mixture is homogenized (300 rpm) for at least 30 minutes.

A 1N NaOH solution is prepared.

A fraction of the 1N NaOH solution is gradually introduced, with stirring (300 to 500 rpm). The mixture is homogenized for 15 minutes.

The ibuprofen is introduced, with stirring (500 rpm), and the mixture is homogenized for 1 hour.

While maintaining the stirring, the remainder of the 1N NaOH solution is added and then the pH (5.4) is checked. The pH is adjusted, if necessary, to 5.4 with the remainder of the 1N NaOH solution.

The mixture is homogenized for 2 hours (300 rpm).

The unit volume is adjusted (150 ml) and the bottles are filled. The stirring is maintained in the 400 liter tank and the buffer tank during the filling of the bottles.

Bottles are removed at the beginning, in the middle and at the end of the filling.

Results

|  | beginning | middle | end |
|---|---|---|---|
| bottle 1 | 99 | 103 | 103.5 |
| bottle 2 | 98.5 | 101.2 | 101.2 |

The content does not vary significantly during the filling. The suspension remains homogeneous.

Tests of stability carried out under accelerated conditions (40° C. and 75% relative humidity)

|  | T 0 | T 1 month | T 3 months |
|---|---|---|---|
| Content (mg/ml) | 19.0 | 20.4 | 19.6 |
| % released | 0.35 | 0.25 | 0.24 |
| Parabens (mg/ml) | 1.07 | 1.15 | 1.09 |

EXAMPLE 2

Suspension of Ibuprofen Crystals

A batch corresponding to 10 000 bottles of 200 ml is prepared in the example below:

| COMPONENTS | |
|---|---|
| Ibuprofen crystals | 40.0 kg |
| Sucrose | 770.666 kg |
| Noncrystallizable sorbitol at 70% | 122 kg |
| Carbopol ® 971 P | 3.446 kg |
| Nipagin ® | 1.707 kg |
| Nipasol ® | 0.253 kg |
| Ethyl hydroxybenzoate | 0.373 kg |
| Strawberry flavor | 2.333 kg |
| Cochineal Red A coloring | 0.067 kg |
| Sodium hydroxide | 0.533 kg |
| Purified water | 1355 kg |

Preparation

The ibuprofen suspension according the same procedure, adapting the material to the size of the batch. A 2 000 liter tank equipped with a jacket is used for the preparation, as well as a 500 liter tank for the preparation of the Carbomer dispersion.

Results

Samples (1 to 12) are collected during the emptying of the 2 000 liter tank.

2 batches of suspension are prepared and the contents are the following:

|  | 1 | 2 | 3 | 4 | 5 | 6 | 7 | 9 | 10 | 12 |
|---|---|---|---|---|---|---|---|---|---|---|
| 58900 | 104 |  | 107.0 | 107.3 | 106 | 103.3 |  | 106 | 107.7 |  |
| 58901 | 106.5 | 106.9 | 105.2 | 102.9 |  | 108.3 | 104.8 | 109.7 | 101.3 | 97.9 |

The contents are homogeneous, contained in the specifications.

EXAMPLE 3

Suspension of Ibuprofen Crystals

The procedure is carried out as in example 1

The suspension is prepared according to the following formula:

| Component | Unit formula 150 ml* | % (w/w) |
|---|---|---|
| Ibuprofen | 3.000 g | 1.71% |
| Sucrose | 57.800 g | 32.93% |
| Noncrystallizable sorbitol at 70% | 9.150 g | 5.21% |
| Carbomers (Carbopol ® 971 P) | 0.260 g | 0.15% |
| Parabens (Nipasept ® base) | 0.175 g | 0.10% |
| Strawberry flavor | 0.175 g | 0.10% |
| Cochineal Red A coloring | 0.005 g | 0.003% |
| Sodium hydroxide | 0.040 | 0.02% |
| Purified water | 104.895 g | 59.78% |

The total parabens representing 0.1% (w/w) of the suspension are a mixture of three para-hydroxybenzoate esters in the following proportions:

73% Methylparaben

16% Ethylparaben

11% Propylparaben

This suspension is subjected to accelerated storage conditions (40° C. and 75% relative humidity).

The results obtained are summarized in the following table.

|  | T 0 | T 6 months |
|---|---|---|
| Content mg/ml | 16.8 | 20.1 |
| % released | 0.51 | 0.21 |

|  | T 6 months |
|---|---|
| Total microorganisms: (CFU/ml) | <1 |
| Yeasts molds CFU/ml | <1 |
| *Escherichia coli*: (CFU/ml) | Absence |

The suspension is stable for six months under these conditions.

Tests of the efficacy of the preservatives

A microbiological test is carried out according to the method described in the European Pharmacopeia 3rd ed.

The test for the suspension of crystals is carried out against a placebo suspension of the same composition but containing no preservative.

suspension with preservatives

|  | Inoculum | T 0 |  | 14 d |  | 28 d |  |
|---|---|---|---|---|---|---|---|
|  | CFU | CFU | RF | CFU | RF | CFU | RF |
| *Pseudo aeruginosa* | $3.30 \times 10^6$ | <100 |  | <10 |  | <10 |  |
| *Staph. Aureus* | $1.26 \times 10^7$ | $1.85 \times 10^4$ |  | <10 |  | <10 |  |
| *E. coli* | $7.90 \times 10^6$ | <100 |  | <10 |  | <10 |  |
| *Candida albicans* | $1.00 \times 10^6$ | $4.85 \times 10^3$ |  | <10 |  | <10 |  |
| *Aspergillus nigers* | $4.65 \times 10^6$ | $5.45 \times 10^5$ |  | $7.10 \times 10^3$ | 2.8 | $4.65 \times 10^3$ | 3.0 |

| Ph Eur. 3rd ed. | Bacteria | Molds | Yeasts | Conclusion |
|---|---|---|---|---|
|  | complies | complies | complies | complies | suspension without preservative

|  | Inoculum | T 0 |  | 14 d |  | 28 d |  |
|---|---|---|---|---|---|---|---|
|  | CFU | CFU | RF | CFU | RF | CFU | RF |
| *Pseudo aeruginosa* | $3.30 \times 10^5$ | $3.85 \times 10^5$ |  | <10 |  | <10 |  |
| *Staph. Aureus* | $1.26 \times 10^7$ | $1.22 \times 10^6$ |  | <10 |  | <10 |  |
| *Candida albicans* | $1.00 \times 10^6$ | $1.02 \times 10^5$ |  | $1.00 \times 10^3$ | 3 | $4.10 \times 10^4$ | 1.4 |
| *Aspergillus nigers* | $4.65 \times 10^6$ | $5.10 \times 10^5$ |  | $3.40 \times 10^4$ | 2.1 | $6.60 \times 10^3$ | 2.8 |

| Ph Eur. 3rd ed. | Bacteria | Molds | Yeasts | Conclusion |
|---|---|---|---|---|
|  | complies | complies | does not comply | does not comply |

The test meets the criteria of the European Pharmacopeia 3rd ed. The total paraben concentration of 0.1% (w/) allows effective protection of the suspension.

EXAMPLE 4

Suspension of Ibuprofen Granules Containing 20 mg/ml of Ibuprofen
Formula of the microgranules:

| Excipients | Quantities (g) | % (w/w) |
|---|---|---|
| Ibuprofen | 1.19 | 9.2 |
| Neutres | 4.64 | 35.7 |
| Eudragit E 100 ® | 0.071 | 0.55 |
| Eudragit NE30D ® | 0.060 | 0.46 |
| Colloidal silica | 0.006 | 0.04 |
| Talc | 0.024 | 0.18 |
| Alcohol 95% (solvent) | 0.52 | — |

The microgranules are prepared by spraying successive layers of active agents followed by a dispersion of coating which makes it possible to mask the bitterness of the active ingredient.

Syrup formula:

| Components | % (w/w) |
|---|---|
| Carbopol ® 971 P | 0.14 |
| Purified water | q.s. 100% |
| Ibuprofen granules | 1.7 |
| NaOH (1N) | q.s. pH = 5.5 |
| Sorbitol at 70% | 3.4 |
| Crystal sucrose | 30.8 |
| Nipasept ® | 0.1 |
| Strawberry flavor | 0.1 |
| [lacuna] | 3 |

The ibuprofen granules having a titer of 200 mg/g are added in order to obtain a suspension at 20 mg/ml of ibuprofen.

The syrup is prepared according to the preceding examples.

EXAMPLE 5

Dry Suspension of Microgranules
The microgranules are prepared as in example 4
2) Formula of the dry adjuvant mixture:

| Excipients | Quantities (g) | % (w/w) |
|---|---|---|
| Carbopol ® 971P | 46.0 | 2.62 |
| Sucrose | 1529 | 87.14 |
| Sorbitol | 153.0 | 8.72 |
| Trisodium citrate | 10.0 | 0.57 |
| Cochineal Red | 0.6 | 0.03 |
| Strawberry flavor | 11.0 | 0.63 |
| Total parabens | 5.0 | 0.29 |
| Total dry mass | 1745.6 | 100% |
| $H_2O$ (wetting liquid) | 120.0 | |

The various dry components are mixed for 15 minutes in a cubic mixer.

The excipients are then granulated by adding purified water to the mixture, for a sufficient period. The granules are dried at 35° C. for 3 hours, and then sized on a screen with a 1.25 mm mesh.

Final preparation: ibuprofen suspension:

| | |
|---|---|
| Microgranules (g) | 6 |
| Dry adjuvant mixture (g) | 7 |
| Quantity of water to be added (ml) | QS 60 ml |
| Ibuprofen per bottle of 60 ml | 1.2 g |

A quantity of sparklets and of granules is added in the proportion defined in the table above.

The suspension is prepared by adding water to the bottle. On stirring vigorously, the granules are dispersed in the liquid phase. After standing for 1 to 2 minutes, the suspension is again stirred. The granules are then homogeneously distributed in the liquid phase and remain in suspension.

EXAMPLE 6

Suspension of Ibuprofen Microgranules

| COMPONENTS | UNIT FORMULA 150 ml bottles | |
|---|---|---|
| | gram | % |
| Ibuprofen microgranules | 15 | 8.5 |
| Carbopol ® 971 P | 0.2 | 0.11 |
| Sucrose | 59.2 | 33.75 |
| Sorbitol | 6.6 | 3.75 |
| Total parabens | 0.06 | 0.1 |
| Strawberry flavor | 0.2 | 0.1 |
| Coloring | <0.01 | <0.01 |
| NaOH1M | qs pH 5.5 | qs pH 5.5 |
| Purified water | qs | qs |

Tests of stability carried out under accelerated conditions (40° C. and 75% relative humidity)

| | T 0 | T 1 month | T 3 months |
|---|---|---|---|
| Content (mg/ml) | 103.3 | 98.1 | 108.2 |
| % released | 0.52 | 0.63 | 0.70 |

| | T 0 | T 1 month | T 3 months |
|---|---|---|---|
| Total microorganisms | <1 | <1 | <1 |
| Yeasts molds | <1 | <1 | <1 |
| *Escherichia coli* | Absence | ND | Absence |

What is claimed is:

1. An oral pharmaceutical ibuprofen suspension which is provided in a dry form, and is reconstituted before use in liquid form, or which is ready for use in liquid form, wherein said suspension comprises a liquid phase in which ibuprofen in a solid state is dispersed and wherein said liquid phase consists of:
   a carbomer as a viscosity agent,
   a filler,
   an alkalinizing agent,
   a flavoring agent,
   a preservative,
   a coloring agent, and
   ibuprofen in the form of crystals or formulated in granules dispersed in the liquid phase, wherein
   (i) said carbomer is between 0.1 and 2.5% by weight relative to the weight of the suspension,
   (ii) said alkalinizing agent is chosen so as to adjust the pH to between 4 and 5.5, and (iii) said filler is between 30 and 55% by weight relative to the weight of the suspension.

2. The oral pharmaceutical suspension as claimed in claim 1, wherein the size of the crystals is less than 500 microns.

3. The oral pharmaceutical suspension as claimed in claim 1, wherein said granules are coated with a polymer material intended to mask the taste of the ibuprofen or to allow the modified release of the ibuprofen.

4. The oral pharmaceutical suspension as claimed in claim 3, wherein the size of said granules is between 50 and 1000 microns.

5. The oral pharmaceutical suspension as claimed in claim 1, wherein said liquid phase is aqueous or consists of a mixture of water and of a miscible cosolvent.

6. The oral pharmaceutical suspension as claimed in claim 1, wherein said suspension contains sucrose or a noncariogenic agent selected from the group consisting of sorbitol, xylitol, mannitol and maltodextrins.

7. The oral pharmaceutical suspension as claimed in claim 1, wherein said preservative is a mixture of antibacterial preservatives, at least one of which is an ester of parabens, and wherein said mixture represents 0.05 to 3% by weight relative to the weight of the suspension.

8. The oral pharmaceutical suspension as claimed in claim 1, wherein said flavoring agent represents 0.1 to 3% by weight relative to the weight of the suspension.

9. The oral pharmaceutical suspension as claimed in claim 1, wherein said suspension contains 0.15% of carbomer and wherein the pH is equal to 5.4.

10. The oral pharmaceutical suspension as claimed in claim 1, wherein said filler is a sucrose or a polyol.

11. The oral pharmaceutical suspension as claimed in claim 7, wherein said mixture represents 0.1 to 1% by weight relative to the weight of the suspension.

* * * * *